United States Patent [19]

Fryer et al.

[11] 4,259,503
[45] Mar. 31, 1981

[54] TRIAZOLE INTERMEDIATES FOR TRIAZOLOBENZAZEPINES

[75] Inventors: Rodney I. Fryer, North Caldwell; Eugene J. Trybulski, Parsippany; Armin Walser, West Caldwell, all of N.J.

[73] Assignee: Hoffmann-La Roche Inc., Nutley, N.J.

[21] Appl. No.: 173,583

[22] Filed: Jul. 30, 1980

Related U.S. Application Data

[62] Division of Ser. No. 99,109, Nov. 30, 1979.

[51] Int. Cl.³ .......................................... C07D 403/06
[52] U.S. Cl. .................................................. 548/255
[58] Field of Search ........................................ 548/255

[56] References Cited

U.S. PATENT DOCUMENTS

| | | | |
|---|---|---|---|
| 3,642,813 | 2/1972 | Kirchmayr et al. | 548/255 |
| 3,813,412 | 5/1974 | Gall et al. | 548/255 |
| 3,897,438 | 7/1975 | Draber et al. | 548/255 |

*Primary Examiner*—Alton D. Rollins
*Attorney, Agent, or Firm*—Jon S. Saxe; Bernard S. Leon; Frank P. Hoffman

[57] ABSTRACT

There is presented triazolobenzazepines of the formula

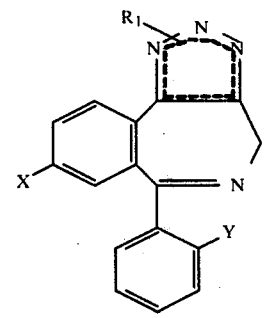

wherein $R_1$ is hydrogen or lower alkyl and X and Y are hydrogen or halogen
and the pharmaceutically acceptable salts thereof.

Also disclosed are novel processes and intermediates leading to the triazolobenzazepines.

The triazolobenzazepines are useful compounds having anxiolytic, sedative, muscle relaxant and anticonvulsant activity.

1 Claim, No Drawings

TRIAZOLE INTERMEDIATES FOR TRIAZOLOBENZAZEPINES

This is a division, of application Ser. No. 99,109 filed Nov. 30, 1979.

DESCRIPTION OF THE INVENTION

The present invention relates to triazolobenzazepines of the formula

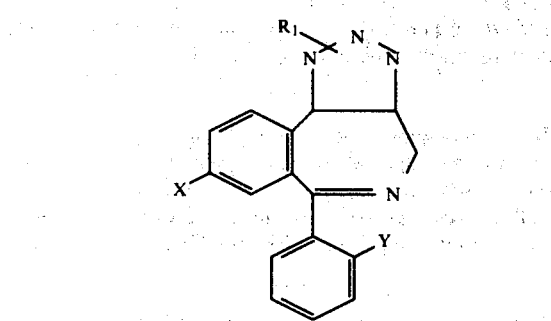

wherein $R_1$ is hydrogen or lower alkyl and X and Y are hydrogen or halogen
and the pharmaceutically acceptable salts thereof.

Particularly preferred compounds are those wherein X is chloro, Y is hydrogen, chloro or fluoro and $R_1$ is hydrogen or methyl with the 2-position as preferred for the methyl substituent along with the 3-position.

As used herein, the term "lower alkyl" means a branched or straight chain hydrocarbon radical of $C_1$ to $C_7$ length with $C_1$ to $C_4$ as preferred, e.g., methyl, ethyl, isopropyl, butyl, etc.

As used herein, the term "halogen" means all four forms thereof, i.e., chloro, bromo, iodo and fluoro.

The following set forth the reaction scheme utilized to produce the novel end products:

Scheme 1

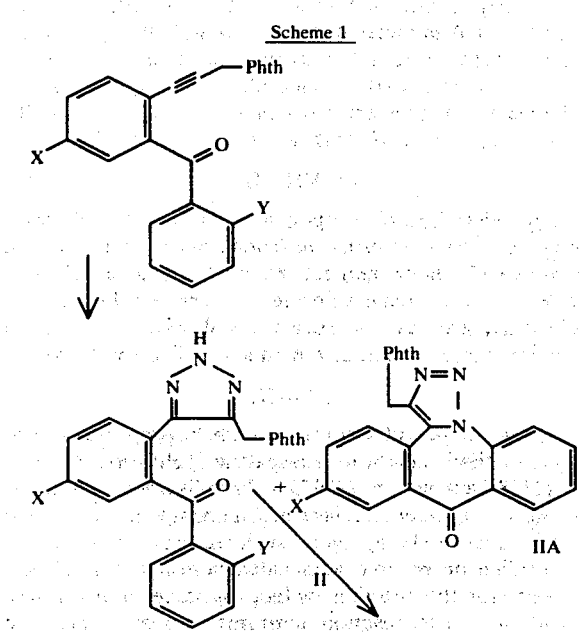

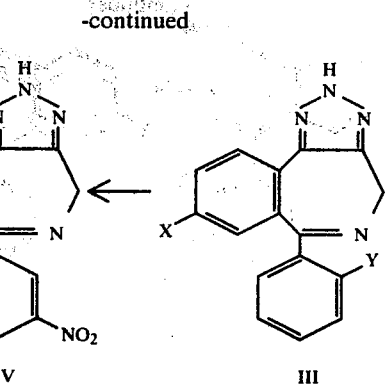

wherein X and Y are as above

Scheme 2

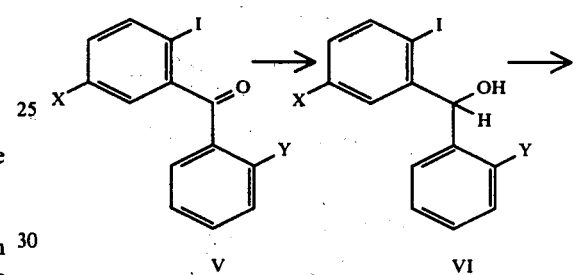

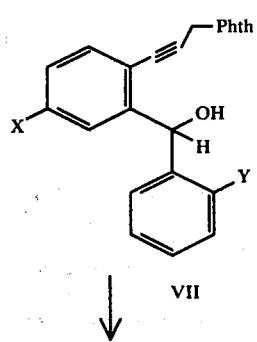

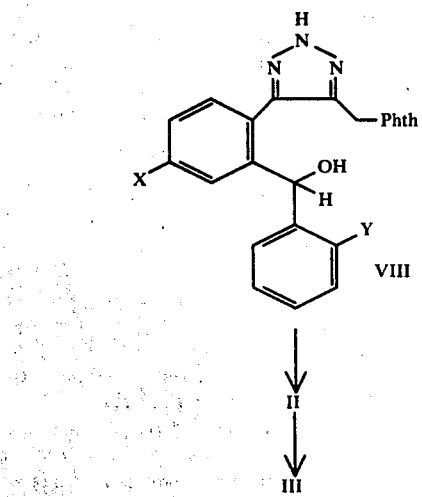

wherein X and Y are as above.

Scheme 3

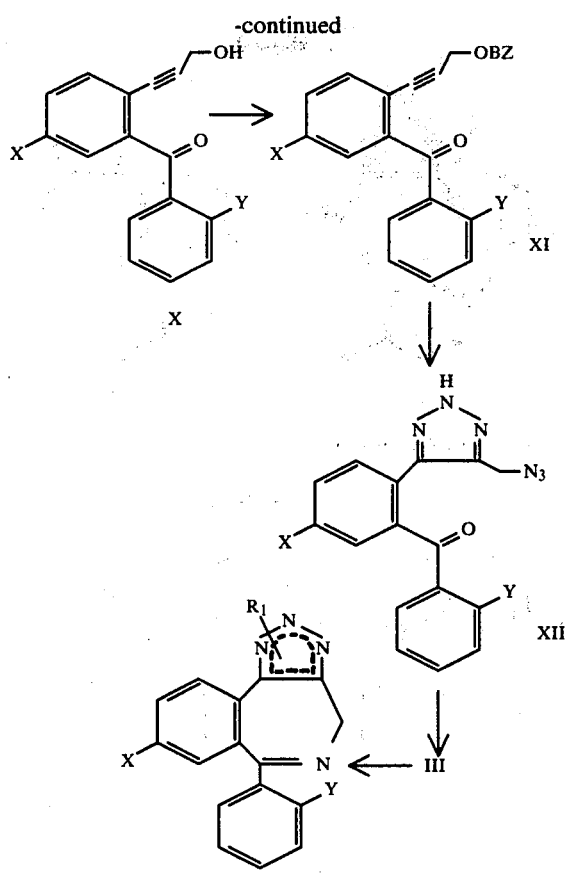

wherein R₁, X and Y are as above

I→II and IIA

The compound of formula I is a previously disclosed compound, see U.S. patent application Ser. No. 10,118, and may be produced following the teaching set forth in Examples 17 to 26. The compound of formula I may be reacted with an alkali metal azide, such as, sodium or potassium azide and a lower alkyl carboxylic acid, such as, acetic or propionic acid, in a polar aprotic solvent, such as, dimethylsulfoxide or dimethylformamide. The reaction temperature may be varied from about room temperature to about 110° C. with the particular preferred temperature chosen dependent on the substitution pattern of the moieties X and Y. The byproduct IIA is thereafter isolated and discarded.

II→III

The compound of formula II is thereafter reacted with an aqueous solution of a lower alkyl amine, e.g., methyl amine. A $C_1$ to $C_4$ alcohol is utilized as the solvent with ethanol as preferred. The reaction is most preferably carried out at about room temperature. The final product is isolated thereafter by utilizing well-known filtration techniques. The first formed open amine is not isolated but undergoes spontaneous ring closure to the first product III.

An alternate method to produce the compound of formula III consists of the reaction of the compound of formula II with hydrazine in an inert solvent, such as, ethanol, a mixture of ethanol and chloroform, tetrahydrofuran or aqueous ethanol. The reaction temperature may vary from about room temperature to about 100° C. with reflux temperature of the selected solvent as preferred. The product is extracted with dilute mineral acid and thereafter recovered and neutralized.

A third method which may be utilized to produce the compound of formula III consists of a base followed by acid hydrolysis of the compound of formula II. For the acid part of the hydrolysis, a 30% solution of a mineral acid such as, hydrochloric, hydrobromic, sulfuric or phosphoric acid may be utilized. The reaction is run at or about reflux temperature. For a base part of the hydrolysis, an alkali metal hydroxide such as potassium or sodium hydroxide is utilized. Inert organic solvents, such as those set forth above may be utilized to solubilize the ingredients. The reaction is run at or near reflux temperature of the selected solvent.

III→IV

The compound of formula III is thereafter reacted with any conventional nitrating agent, for example, an alkali metal nitrate, such as, sodium or potassium nitrate in sulfuric acid. The reaction is carried out from about 0° C. to about room temperature with 0° C. as preferred.

V→VI

The compound of formula V is reduced by utilizing a metal hydride reducing agent such as sodium borohydride in an alcoholic solvent, such as, ethanol or methanol or lithium aluminum hydride in an ethereal solvent, such as, tetrahydrofuran or dioxane. The reaction temperature may range from about −10° C. to about room temperature with about 0° C. as preferred.

VI→VII

The compound of formula VI is thereafter reacted with a combination of palladium chloride, cuprous iodide, triphenylphosphine and propargylphthalimide in a solvent, such as, methylene chloride or dimethylformamide utilizing as a base a di- or tri- alkylamine, e.g., diethylamine, triethylamine. The above reaction may be run at from about 0° C. to about 40° C. with about room temperature as preferred.

VII→VIII

A compound of formula VII is thereafter reacted with an alkali metal azide and a lower alkyl carboxylic acid in the pressure of an inert polar aprotic solvent, such as, dimethylsulfoxide and dimethylformamide. The reaction temperature may be varied from about 60° C. to about 100° C. with about 90° C. as preferred.

VII→II

The benzhydrol compound of formula VIII is thereafter oxidized utilizing an oxidizing agent such as the Jones or Collins reagent in an inert organic solvent, such as, methylene chloride or acetone. The reaction temperature may be varied from about −10° C. to about room temperature with about 0° C. preferred.

X→XI

The compound of formula X can be prepared following methods taught in U.S. patent application Ser. No. 10,118 filed on Feb. 7, 1979 to Trybulski which is incorporated by reference herein. The compound is reacted with a benzoylating agent, such as, benzoyl chloride in pyridine or benzoic acid anhydride in pyridine. Solvents for the reaction include pyridine or methylene chloride. The reaction temperature may vary from about 0° C. to about room temperature with room temperature as preferred.

XI→XII

The compound of formula XI is thereafter reacted with an alkali metal azide, such as, sodium or potassium azide in the presence of an inert polar aprotic solvent such as dimethylformamide or dimethylsulfoxide. The reaction may be run at from about room temperature to about 100° C. with about 80° C. as preferred.

XII→III

The compound of formula XII is thereafter hydrogenated in the presence of a transition metal catalyst, such as Raney nickel or Platinum oxide and, if desired, in the presence of a mineral acid, such as, hydrochloric acid. The reaction takes place at about room temperature and at a pressure which may be varied from atmospheric pressure to about 40 psi with atmospheric pressure preferred.

III→XIII

The compound of formula III is thereafter treated with an alkali metal hydroxide, e.g., sodium or potassium hydroxide in a $C_1$ to $C_6$ alcohol, preferably a $C_1$ to $C_4$ alcohol. Subsequently the resultant mixture is reacted with a suitable alkylating agent such as a dialkyl sulfate, e.g. dimethylsulfate, an alkyl halide, e.g. methyl chloride or an alkyl tosylate. The reaction may be carried out from about 0° C. to about room temperature with about room temperature preferred.

The major product in the alkylation was assigned to the 2-position isomer. A minor product was isolated and assigned to the 3-position isomer.

The expression "pharmaceutically acceptable salts" is used to include both inorganic and organic pharmaceutically acceptable strong acids, such as, sulfuric acid, hydrochloric acid, nitric acid, methanesulfonic acid and paratoluenesulfonic acid. Such salts can be formed quite readily by those skilled in the art with the prior art and the nature of the compound to be placed in salt form in view.

The following examples are illustrative of the present invention and are not intended to limit the scope thereof.

EXAMPLE 1

4-[4-Chloro-2-benzoylphenyl]-5-[N-phthalimidomethyl]-2H-1,2,3-triazole

A mixture of 20 g (0.05 mole) of 1-[4-chloro-2-benzoylphenyl]-3-phthalimidopropyne, 15.0 g (0.23 mole) of sodium azide and 3.0 ml (0.05 mole) of acetic acid in 300 ml of dimethyl sulfoxide was heated to 90° C. for 3 days. The mixture was cooled, diluted with 1.5 L of water and 250 ml of methylene chloride. The mixture was extracted with ether and the combined ether extracts washed with water. The ether solution was dried with anhydrous sodium sulfate and concentrated at reduced pressure to give crude end product. Recrystallization from a mixture of methylene chloride and ether gave colorless needles, mp 134°-136° C.

EXAMPLE 2

4-[4-Chloro-2-(2-fluorobenzoyl)phenyl]-5-[N-phthalimidomethyl]-2H-1,2,3-triazole A mixture of 10 g (24 mmole) of 1-[4-chloro-2-(2-fluorobenzoyl)phenyl]-3-phthalimidopropyne, 7.5 g (115 mmole) of sodium azide, 2.2 ml (36 mmole) of acetic acid and 150 ml of dimethyl sulfoxide was heated to 50° for 48 hr. The mixture was cooled, diluted with water, and the resulting precipitate collected by filtration to give 11.0 g of the crude mixture. Purification by column chromatography (silica gel, 105 g; eluent methylene chloride to 5% ether in methylene chloride gradient) gave as the first major component fine prisms, mp 252°-253° C. and the title compound as the second component as light sensitive prisms, mp 147°-148° C. (foams).

EXAMPLE 3

4-[4-Chloro-2-(2-chlorobenzoyl)phenyl]-5-[N-phthalimidomethyl]-2H-1,2,3-triazole A mixture of 6.8 g (15.6 mmole) of 1-[4-chloro-2-(2-chlorobenzoyl)phenyl]-3-phthalimidopropyne, 5.0 g (85 mmole) of sodium azide, 1.0 ml (17 mmole) of acetic acid, and 75 ml of dimethyl sulfoxide was heated to 50° C. for 48 hr. The mixture was cooled, diluted with water, and extracted with methylene chloride. The methylene chloride solution was washed with water, dried with anhydrous sodium sulfate, and concentrated at reduced pressure to give 6.5 g of a yellow foam. Purification by column chromatography (silica gel, 40 g; eluent, methylene chloride to 5% ether in methylene chloride gradient) gave colorless prisms, mp 186°-187° C.

EXAMPLE 4

4-[2-(2-Chlorobenzoyl)phenyl]-5-[N-phthalimidomethyl]-2H-1,2,3-triazole

A mixture of 10.0 g (25 mmole) of 1-[2-(2-chlorobenzoyl)phenyl]-3-phthalimidopropyne, 7.5 g (115 mmole) of sodium azide, 1.5 ml (25 mmole) of acetic acid and 150 ml of dimethyl sulfoxide was heated to 90° C. for 24 hr. The mixture was cooled, diluted with water, and extracted with methylene chloride. The methylene chloride solution was washed with water, dried with anhydrous sodium sulfate, and concentrated at reduced pressure to give a brown oil. Trituration with a mixture of ether and petroleum ether gave cream colored prisms, mp 105°-106° C. (foams).

EXAMPLE 5

4-[2-Benzoylphenyl]-5-[N-phthalimidomethyl]-2H-1,2,3-triazole

A mixture of 10.0 g (27.0 mmole) of 1-(2-benzoylphenyl)-3-phthalimidopropyne, 7.5 g (115 mmole) of sodium azide, 1.5 ml (25 mmole) of acetic acid, and 150 ml of dimethyl sulfoxide was heated to 90° C. for 60 hr. The mixture was cooled, diluted with water, and extracted with methylene chloride. The methylene chloride solution was washed with water, dried with anhydrous sodium sulfate, and concentrated at reduced pressure to give a brown oil. Crystallization with ether gave tan crystals. Recrystallization from a mixture of ether and methylene chloride gave white prisms, mp 204°-205° C.

EXAMPLE 6

8-Chloro-6-phenyl-2H,4H-[1,2,3]triazolo[4,5-d][2]benzazepine

A mixture of 6.0 g (13.6 mmole) of 4-[4-chloro-2-benzoylphenyl]-5-[N-phthalimidomethyl]-2H-1,2,3-triazole, 50 ml of 40% aqueous methylamine, and 100 ml of 95% ethanol was stirred at room temperature for 12 hr. The solvents were removed at reduced pressure, and the residue was triturated with a 2 to 1 mixture of ether and methylene chloride. The resulting precipitate was removed by filtration, and the filtrate was washed with water and dried with anhydrous sodium sulfate. Concentration of the ether solution at reduced pressure gave colorless prisms, mp 199°–200° C.

EXAMPLE 7

8-Chloro-6-(2-fluorophenyl)-2H,4H-[1,2,3]triazolo[4,5-d][2]benzazepine

The preparation of 8-chloro-6-(2-fluorophenyl)-2H,4H-[1,2,3]triazolo[4,5-d]benzazepine was conducted in the same manner as the preparation of 8-chloro-6-phenyl-2H,4H-[1,2,3]triazolo[4,5-d][2]benzazepine to give a colorless solid, mp 192°–193° C.

The methanesulfonate salt of 8-chloro-6-(2-fluorophenyl)-2H,4H-[1,2,3]triazolo[4,5-d][2]benzazepine was prepared by adding equimolar amounts of the above compound and methanesulfonic acid to methanol, and isolated by precipitating the salt with the addition of ether. Recrystallization from a mixture of methanol and ether gave the methanesulfonate salt as yellow prisms, mp 237°–238° C.

EXAMPLE 8

8-Chloro-6-(2-chlorophenyl)-2H,4H-[1,2,3]triazolo[4,5-d][2]benzazepine

The preparation of 8-chloro-6-(2-chlorophenyl)-2H,4H-[1,2,3]triazolo[4,5-d][2]benzazepine was conducted in the same manner as the preparation of 8-chloro-6-phenyl-2H,4H-[1,2,3]triazolo[4,5-d][2]benzazepine to give colorless prisms, mp 176°–177° C.

The methanesulfonate salt of 8-chloro-6-(2-chlorophenyl)-2H,4H-[1,2,3]triazolo[4,5-d][2]benzazepine was prepared by adding equimolar amounts of the above compound and methanesulfonic acid to methanol and isolated by precipitating the salt with the addition of ether. Recrystallization from a mixture of methanol and ether gave the methanesulfonate salt as yellow prisms, mp 236°–237° C.

EXAMPLE 9

6-(2-Chlorophenyl)-2H,4H-[1,2,3]triazolo[4,5-d][2]benzazepine

The preparation of 6-(2-chlorophenyl)-2H,4H-[1,2,3]triazolo[4,5-d][2]benzazepine was conducted in the same manner as the preparation of 8-chloro-6-phenyl-2H,4H-[1,2,3]triazolo[4,5-d][2]benzazepine to give colorless prisms, mp 191°–193° C.

The methanesulfonate salt of 6-(2-chlorophenyl)-2H,4H-[1,2,3]triazolo[4,5-d][2]benzazepine was prepared by adding equimolar amounts of the above compound and methanesulfonic acid to methanol and isolated by precipitating the salt with the addition of ether. Recrystallization from a mixture of methanol and ether gave the methanesulfonate salt as yellow needles, mp 238°–240° C.

EXAMPLE 10

6-Phenyl-2H,4H-[1,2,3]triazolo[4,5-d][2]benzazepine

The preparation of 6-phenyl-2H,4H-[1,2,3]triazolo[4,5-d][2]benzazepine was conducted in the same manner as the preparation of 8-chloro-6-phenyl-2H,4H-[1,2,3]triazolo[4,5-d][2]benzazepine to give colorless prisms, mp 205°–207° C.

The methanesulfonate salt of 6-phenyl-2H,4H-[1,2,3]triazolo[4,5-d][2]benzazepine was prepared by adding equimolar amounts of the above compound and methanesulfonic acid to methanol, and isolated by precipitating the salt with the addition of ether. Recrystallization from a mixture of methanol and ether gave the methanesulfonic salt as yellow prisms, mp 169°–170° C.

EXAMPLE 11

4-{4-Chloro-2-[(2-fluorophenyl)hydroxymethyl]-phenyl}-5-(N-phthalimidomethyl)-2H-1,2,3-triazole A mixture of 1.5 g (3.5 mmole) of 1-{4-chloro-2-[(2-fluorophenyl)hydroxymethyl]phenyl}-3-phthalimidopropyne, 2.0 g (30 mmole) of sodium azide and 0.4 ml (6.6 mmole) of acetic acid in 30 ml of dimethyl sulfoxide was heated in an oil bath to 90° C. for 4 days. The mixture was cooled, diluted with water and the resulting precipitate collected by filtration to give a yellow solid. A sample of the yellow solid was recrystallized from ether to give off-white prisms, mp 160°–162° C.

EXAMPLE 12

4-[4-Chloro-2-(2-fluorobenzoyl)phenyl]-5-[N-phthalimidomethyl]-2H-1,2,3-triazole A solution of 2.67 M Jones reagent (5 ml, 13.3 mmole) was added dropwise to a solution of 1.0 g (2.1 mmole) of 4-{4-chloro-2-[(2-fluorophenyl)hydroxymethyl]-phenyl}-5-(N-phthalimidomethyl)-2H-1,2,3-triazole in 20 ml of acetone. The mixture was stirred at room temperature for 1 hr and the excess Jones reagent was discharged by the addition of isopropanol. The acetone solution was decanted and the acetone removed at reduced pressure. The residue was dissolved in methylene chloride, washed with water and dried over anhydrous sodium sulfate. Concentration of the methylene chloride solution gave, after trituration of the residue with ether, the end product, (mp 133°–135° C., foams) which was identical in every respect to an authentic sample.

EXAMPLE 13

6-(3-Nitrophenyl)-2H,4H-[1,2,3]triazolo[4,5-d][2]benzazepine

A mixture of 1.6 g (4.5 mmole) of the methanesulfonate salt of 6-phenyl-2H,4H-[1,2,3]triazolo[4,5-d][2]benzazepine, 8.6 g of potassium nitrate, and 20 ml of sulfuric acid was stirred at 0° C. for 3.5 hr. The mixture was poured over ice, basified with ammonium hydroxide and extracted with methylene chloride. The methylene chloride solution was dried with anhydrous sodium sulfate and concentrated at reduced pressure. The residue was triturated with ether to give tan crystals (mp 223°–225° C.). Recrystallization from methylene chloride gave cream colored prisms, mp 224°–225° C.

EXAMPLE 14

4-Azidomethyl-5-[4-chloro-2-(benzoyl)phenyl]-2H-1,2,3-triazole

A mixture of 5.9 g (16 mmole) of 3-benzoyloxy-1-[4-chloro-2-(benzoyl)phenyl]propyne, 5.2 g (80 mmole) of sodium azide and 210 ml of N,N-dimethylformamide was heated in an oil bath to 80°–90° C. for 30 hr. After cooling, the mixture was poured into 520 ml of ice water and extracted with methylene chloride. The methylene chloride solution was washed with water, about 0° C. to about room temperature with room temperature as preferred.

XI→XII

The compound of formula XI is thereafter reacted with an alkali metal azide, such as, sodium or potassium azide in the presence of an inert polar aprotic solvent such as dimethylformamide or dimethylsulfoxide. The reaction may be run at from about room temperature to about 100° C. with about 80° C. as preferred.

XII→III

The compound of formula XII is thereafter hydrogenated in the presence of a transition metal catalyst, such as Raney nickel or Platinum oxide and, if desired, in the presence of a mineral acid, such as, hydrochloric acid. The reaction takes place at about room temperature and at a pressure which may be varied from atmospheric pressure to about 40 psi with atmospheric pressure preferred.

III→XIII

The compound of formula III is thereafter treated with an alkali metal hydroxide, e.g., sodium or potassium hydroxide in a $C_1$ to $C_6$ alcohol, preferably a $C_1$ to $C_4$ alcohol. Subsequently the resultant mixture is reacted with a suitable alkylating agent such as a dialkyl sulfate, e.g. dimethylsulfate, an alkyl halide, e.g. methyl chloride or an alkyl tosylate. The reaction may be carried out from about 0° C. to about room temperature with about room temperature preferred.

The major product in the alkylation was assigned to the 2-position isomer. A minor product was isolated and assigned to the 3-position isomer.

The expression "pharmaceutically acceptable salts" is used to include both inorganic and organic pharmaceutically acceptable strong acids, such as, sulfuric acid, hydrochloric acid, nitric acid, methanesulfonic acid and paratoluenesulfonic acid. Such salts can be formed quite readily by those skilled in the art with the prior art and the nature of the compound to be placed in salt form in view.

The following examples are illustrative of the present invention and are not intended to limit the scope thereof.

EXAMPLE 1

4-[4-Chloro-2-benzoylphenyl]-5-[N-phthalimidomethyl]-2H-1,2,3-triazole

A mixture of 20 g (0.05 mole) of 1-[4-chloro-2-benzoylphenyl]-3-phthalimidopropyne, 15.0 g (0.23 mole) of sodium azide and 3.0 ml (0.05 mole) of acetic acid in 300 ml of dimethyl sulfoxide was heated to 90° C. for 3 days. The mixture was cooled, diluted with 1.5 L of water and 250 ml of methylene chloride. The mixture was extracted with ether and the combined ether extracts washed with water. The ether solution was dried with anhydrous sodium sulfate and concentrated at reduced pressure to give crude end product. Recrystallization from a mixture of methylene chloride and ether gave colorless needles, mp 134°–136° C.

EXAMPLE 2

4-[4-Chloro-2-(2-fluorobenzoyl)phenyl]-5-[N-phthalimidomethyl]-2H-1,2,3-triazole A mixture of 10 g (24 mmole) of 1-[4-chloro-2-(2-fluorobenzoyl)phenyl]-3-phthalimidopropyne, 7.5 g (115 mmole) of sodium azide, 2.2 ml (36 mmole) of acetic acid and 150 ml of dimethyl sulfoxide was heated to 50° for 48 hr. The mixture was cooled, diluted with water, and the resulting precipitate collected by filtration to give 11.0 g of the crude mixture. Purification by column chromatography (silica gel, 105 g; eluent methylene chloride to 5% ether in methylene chloride gradient) gave as the first major component fine prisms, mp 252°–253° C. and the title compound as the second component as light sensitive prisms, mp 147°–148° C. (foams).

EXAMPLE 3

4-[4-Chloro-2-(2-chlorobenzoyl)phenyl]-5-[N-phthalimidomethyl]-2H-1,2,3-triazole A mixture of 6.8 g (15.6 mmole) of 1-[4-chloro-2-(2-chlorobenzoyl)phenyl]-3-phthalimidopropyne, 5.0 g (85 mmole) of sodium azide, 1.0 ml (17 mmole) of acetic acid, and 75 ml of dimethyl sulfoxide was heated to 50° C. for 48 hr. The mixture was cooled, diluted with water, and extracted with methylene chloride. The methylene chloride solution was washed with water, dried with anhydrous sodium sulfate, and concentrated at reduced pressure to give 6.5 g of a yellow foam. Purification by column chromatography (silica gel, 40 g; eluent, methylene chloride to 5% ether in methylene chloride gradient) gave colorless prisms, mp 186°–187° C.

EXAMPLE 4

4-[2-(2-Chlorobenzoyl)phenyl]-5-[N-phthalimidomethyl]-2H-1,2,3-triazole

A mixture of 10.0 g (25 mmole) of 1-[2-(2-chlorobenzoyl)phenyl]-3-phthalimidopropyne, 7.5 g (115 mmole) of sodium azide, 1.5 ml (25 mmole) of acetic acid and 150 ml of dimethyl sulfoxide was heated to 90° C. for 24 hr. The mixture was cooled, diluted with water, and extracted with methylene chloride. The methylene chloride solution was washed with water, dried with anhydrous sodium sulfate, and concentrated at reduced pressure to give a brown oil. Trituration with a mixture of ether and petroleum ether gave cream colored prisms, mp 105°–106° C. (foams).

EXAMPLE 5

4-[2-Benzoylphenyl]-5-[N-phthalimidomethyl]-2H-1,2,3-triazole

A mixture of 10.0 g (27.0 mmole) of 1-(2-benzoylphenyl)-3-phthalimidopropyne, 7.5 g (115 mmole) of sodium azide, 1.5 ml (25 mmole) of acetic acid, and 150 ml of dimethyl sulfoxide was heated to 90° C. for 60 hr. The mixture was cooled, diluted with water, and extracted with methylene chloride. The methylene chloride solution was washed with water, dried with anhydrous sodium sulfate, and concentrated at reduced pressure to give a brown oil. Crystallization with ether gave tan crystals. Recrystallization from a mixture of ether and methylene chloride gave white prisms, mp 204°–205° C.

EXAMPLE 6

8-Chloro-6-phenyl-2H,4H-[1,2,3]triazolo[4,5-d][2]benzazepine

A mixture of 6.0 g (13.6 mmole) of 4-[4-chloro-2-benzoylphenyl]-5-[N-phthalimidomethyl]-2H-1,2,3-triazole, 50 ml of 40% aqueous methylamine, and 100 ml of 95% ethanol was stirred at room temperature for 12 hr. The solvents were removed at reduced pressure, and the residue was triturated with a 2 to 1 mixture of ether and methylene chloride. The resulting precipitate was removed by filtration, and the filtrate was washed with water and dried with anhydrous sodium sulfate. Concentration of the ether solution at reduced pressure gave colorless prisms, mp 199°–200° C.

EXAMPLE 7

8-Chloro-6-(2-fluorophenyl)-2H,4H-[1,2,3]triazolo[4,5-d][2]benzazepine

The preparation of 8-chloro-6-(2-fluorophenyl)-2H,4H-[1,2,3]triazolo[4,5-d]benzazepine was conducted in the same manner as the preparation of 8-chloro-6-phenyl-2H,4H-[1,2,3]triazolo[4,5-d][2]benzazepine to give a colorless solid, mp 192°–193° C.

The methanesulfonate salt of 8-chloro-6-(2-fluorophenyl)-2H,4H-[1,2,3]triazolo[4,5-d][2]benzazepine was prepared by adding equimolar amounts of the above compound and methanesulfonic acid to methanol, and isolated by precipitating the salt with the addition of ether. Recrystallization from a mixture of methanol and ether gave the methanesulfonate salt as yellow prisms, mp 237°–238° C.

EXAMPLE 8

8-Chloro-6-(2-chlorophenyl)-2H,4H-[1,2,3]triazolo[4,5-d][2]benzazepine

The preparation of 8-chloro-6-(2-chlorophenyl)-2H,4H-[1,2,3]triazolo[4,5-d][2]benzazepine was conducted in the same manner as the preparation of 8-chloro-6-phenyl-2H,4H-[1,2,3]triazolo[4,5-d][2]benzazepine to give colorless prisms, mp 176°–177° C.

The methanesulfonate salt of 8-chloro-6-(2-chlorophenyl)-2H,4H-[1,2,3]triazolo[4,5-d][2]benzazepine was prepared by adding equimolar amounts of the above compound and methanesulfonic acid to methanol and isolated by precipitating the salt with the addition of ether. Recrystallization from a mixture of methanol and ether gave the methanesulfonate salt as yellow prisms, mp 236°–237° C.

EXAMPLE 9

6-(2-Chlorophenyl)-2H,4H-[1,2,3]triazolo[4,5-d][2]benzazepine

The preparation of 6-(2-chlorophenyl)-2H,4H-[1,2,3]triazolo[4,5-d][2]benzazepine was conducted in the same manner as the preparation of 8-chloro-6-phenyl-2H,4H-[1,2,3]triazolo[4,5-d][2]benzazepine to give colorless prisms, mp 191°–193° C.

The methanesulfonate salt of 6-(2-chlorophenyl)-2H,4H-[1,2,3]triazolo[4,5-d][2]benzazepine was prepared by adding equimolar amounts of the above compound and methanesulfonic acid to methanol and isolated by precipitating the salt with the addition of ether. Recrystallization from a mixture of methanol and ether gave the methanesulfonate salt as yellow needles, mp 238°–240° C.

EXAMPLE 10

6-Phenyl-2H,4H-[1,2,3]triazolo[4,5-d][2]benzazepine

The preparation of 6-phenyl-2H,4H-[1,2,3]triazolo[4,5-d][2]benzazepine was conducted in the same manner as the preparation of 8-chloro-6-phenyl-2H,4H-[1,2,3]triazolo[4,5-d][2]benzazepine to give colorless prisms, mp 205°–207° C.

The methanesulfonate salt of 6-phenyl-2H,4H-[1,2,3]triazolo[4,5-d][2]benzazepine was prepared by adding equimolar amounts of the above compound and methanesulfonic acid to methanol, and isolated by precipitating the salt with the addition of ether. Recrystallization from a mixture of methanol and ether gave the methanesulfonic salt as yellow prisms, mp 169°–170° C.

EXAMPLE 11

4-{4-Chloro-2-[(2-fluorophenyl)hydroxymethyl]phenyl}-5-(N-phthalimidomethyl)-2H-1,2,3-triazole A mixture of 1.5 g (3.5 mmole) of 1-{4-chloro-2-[(2-fluorophenyl)hydroxymethyl]phenyl}-3-phthalimidopropyne, 2.0 g (30 mmole) of sodium azide and 0.4 ml (6.6 mmole) of acetic acid in 30 ml of dimethyl sulfoxide was heated in an oil bath to 90° C. for 4 days. The mixture was cooled, diluted with water and the resulting precipitate collected by filtration to give a yellow solid. A sample of the yellow solid was recrystallized from ether to give off-white prisms, mp 160°–162° C.

EXAMPLE 12

4-[4-Chloro-2-(2-fluorobenzoyl)phenyl]-5-[N-phthalimidomethyl]-2H-1,2,3-triazole A solution of 2.67 M Jones reagent (5 ml, 13.3 mmole) was added dropwise to a solution of 1.0 g (2.1 mmole) of 4-{4-chloro-2-[(2-fluorophenyl)hydroxymethyl]phenyl}-5-(N-phthalimidomethyl)-2H-1,2,3-triazole in 20 ml of acetone. The mixture was stirred at room temperature for 1 hr and the excess Jones reagent was discharged by the addition of isopropanol. The acetone solution was decanted and the acetone removed at reduced pressure. The residue was dissolved in methylene chloride, washed with water and dried over anhydrous sodium sulfate. Concentration of the methylene chloride solution gave, after trituration of the residue with ether, the end product, (mp 133°–135° C., foams) which was identical in every respect to an authentic sample.

EXAMPLE 13

6-(3-Nitrophenyl)-2H,4H-[1,2,3]triazolo[4,5-d][2]benzazepine

A mixture of 1.6 g (4.5 mmole) of the methanesulfonate salt of 6-phenyl-2H,4H-[1,2,3]triazolo[4,5-d][2]benzazepine, 8.6 g of potassium nitrate, and 20 ml of sulfuric acid was stirred at 0° C. for 3.5 hr. The mixture was poured over ice, basified with ammonium hydroxide and extracted with methylene chloride. The methylene chloride solution was dried with anhydrous sodium sulfate and concentrated at reduced pressure. The residue was triturated with ether to give tan crystals (mp 223°–225° C.). Recrystallization from methylene chloride gave cream colored prisms, mp 224°–225° C.

EXAMPLE 14

4-Azidomethyl-5-[4-chloro-2-(benzoyl)phenyl]-2H-1,2,3-triazole

A mixture of 5.9 g (16 mmole) of 3-benzoyloxy-1-[4-chloro-2-(benzoyl)phenyl]propyne, 5.2 g (80 mmole) of sodium azide and 210 ml of N,N-dimethylformamide was heated in an oil bath to 80°–90° C. for 30 hr. After cooling, the mixture was poured into 520 ml of ice water and extracted with methylene chloride. The methylene chloride solution was washed with water, dried with anhydrous sodium sulfate, and concentrated at reduced pressure. The residual oil was crystallized from a mixture of methylene chloride and hexane to give light tan crystals. Recrystallization from a mixture of methylene chloride and hexane gave off-white crystals, mp 128°–131° C.

EXAMPLE 15

8-Chloro-6-phenyl-2H,4H-[1,2,3]triazolo[4,5-d][2]benzazepine

A mixture of 3 g (8.9 mmole) of 4-azidomethyl-5-[4-chloro-2-(benzoyl)phenyl]-2H-1,2,3-triazole and about 3 teaspoonsful of Raney nickel in 150 ml of ethanol was shaken in a Parr bottle with an initial hydrogen pressure of 5 p.s.i. for 1 hr. The catalyst was removed by filtration and the filtrate was concentrated at reduced pressure to give 2 g of gummy solid. The residue was chromatographed over silica gel using a 1:1 mixture of ethyl acetate and methylene chloride as eluent. Evaporation of the solvent gave a gum which crystallized from a small amount of ethyl acetate to give white crystals. Recrystallization from a mixture of ethyl acetate and petroleum ether gave colorless prisms, mp 203°–205° C.

EXAMPLE 16

5-Chloro-2-iodobenzophenone

A mixture of 76 g (1.1 mole) of sodium nitrite and 450 ml of sulfuric acid was heated on a steam bath to ca 80° until complete solution was achieved. The solution was cooled to 30° and 232 g (1.0 mole) of 2-amino-5-chlorobenzophenone was added in portions keeping the temperature between 30° and 40°. The mixture was stirred for 1 hr and then slowly poured into 3 L of an ice and water mixture. The solution was filtered through Hy-Flo and to the stirred filtrate was added slowly a solution of 200 g (1.83 mole) of sodium fluoborate in 800 ml of water. The resulting precipitate was collected by filtration and washed with water (2×100 ml) to give a moist white solid.

The moist 2-benzoyl-4-chlorobenzenediazonium fluoborate was slurried in 3 L of water, and a solution of 332 g (2 moles) of potassium iodide in 1 L of water was added dropwise. The mixture was stirred at room temperature for 4 hr and the resulting precipitate was collected by filtration. The crude product was added to 1 L of boiling ether, filtered, and dried with anhydrous sodium sulfate. The ether solution was concentrated to 500 ml and the addition of 100 ml of petroleum ether gave end product. A small amount of end product was recrystallized from a mixture of ether and petroleum ether to give light yellow prisms, mp 80°–82°.

EXAMPLE 17

5-Chloro-2'-fluoro-2-iodobenzophenone

The preparation of 5-chloro-2'-fluoro-2-iodobenzophenone was conducted in the same manner as the preparation of 5-chloro-2-iodobenzophenone to give the end product as light yellow prisms, mp 78°–81°.

EXAMPLE 18

2',5'-Dichloro-2-iodobenzophenone

The preparation of 2'-5-dichloro-2-iodobenzophenone was conducted in the same manner as the preparation of 5-chloro-2-iodobenzophenone to give the end product as light yellow prisms, mp 64°–66°.

EXAMPLE 19

2-Iodobenzophenone

The preparation of 2-iodobenzophenone was conducted in the same manner as the preparation of 5-chloro-2-iodobenzophenone to give the end product as a brown oil. A small amount was purified by column chromatography to give the end product as white prisms, mp 29°–31°.

EXAMPLE 20

2'-Chloro-2-iodobenzophenone

The preparation of 2'-chloro-2-iodobenzophenone was conducted in the same manner as the preparation of 5-chloro-2-iodobenzophenone to give the end product as pale yellow prisms, mp 62°–64°.

EXAMPLE 21

1-[4-Chloro-2-benzoylphenyl]-3-phthalimidopropyne

A mixture of 0.71 g (4.0 mmole) of palladium chloride, 2.1 g (8.0 mmole) of triphenylphosphine, 0.80 g (4.2 mmole) of cuprous iodide, 68.8 g (0.20 mole) of 5-chloro-2-iodobenzophenone, 200 ml of diethylamine, and 400 ml of methylene chloride was stirred at room temperature under argon until complete solution was obtained. In one portion, 40.0 g (0.22 mole) of N-propargylphthalimide was added to the solution and the resulting mixture stirred for 20 hr. The volatiles were removed at reduced pressure and the residue was triturated with 200 ml of iospropanol. The resulting precipitate was collected by filtration to give crude end product. Recrystallization from acetone gave cream colored prisms, mp 148°–150° C.

EXAMPLE 22

1-[4-Chloro-2-(2-fluorobenzoyl)phenyl]-3-phthalimidopropyne

The preparation of 1-[4-chloro-2-(2-fluorobenzoyl)phenyl]-3-phthalimidopyropyne was conducted in a similar manner as the preparation of 1-[4-chloro-2-benzoylphenyl]-3-phthalimidopropyne to give cream colored prisms, mp 158°–161° C.

EXAMPLE 23

1-[4-Chloro-2-(2-chlorobenzoyl)phenyl]-3-phthalimidopropyne

The preparation of 1-[4-chloro-2-(2-chlorobenzoyl)phenyl]-3-phthalimidopropyne was conducted in the same manner as the preparation of 1-[4-chloro-2-benzoylphenyl]-3-phthalimidopropyne to give cream colored prisms, mp 144°–145° C.

EXAMPLE 24

1-[2-(2-chlorobenzoyl)phenyl]-3-phthalimidopropyne

The preparation of 1-[2-(2-chlorobenzoyl)phenyl]-3-phthalimidopropyne was conducted in the same manner as the preparation of 1-[4-chloro-2-benzoylphenyl]-3-phthalimidopropyne to give cream colored prisms, mp 149°–150° C.

EXAMPLE 25

1-[2-benzoylphenyl]-3-phthalimidopropyne

The preparation of 1-[2-benzoylphenyl]-3-phthalimidopropyne was conducted in the same manner as the preparation of 1-[4-chloro-2-benzoylphenyl]-3- phthalimidopropyne to give cream colored prisms, mp 164°–165° C.

EXAMPLE 26

8-Chloro-6-(2-fluorophenyl)-2-methyl-2H,4H-[1,2,3]triazolo[3,4-d][2]benzazepine (A) and
8-Chloro-6-(2-fluorophenyl)-3-methyl-2H,4H-[1,2,3]triazolo[3,4-d][2]benzazepine (B)

A mixture of 2.6 g (9.4 mmol) of 8-chloro-6-(2-fluorophenyl)-2H,4H-[1,2,3]triazolo[3,4-d][2]benzazepine, 2.0 mL (21 mmol) of dimethylsulfate and 10 mL of 3 N aqueous sodium hydroxide in 25 mL of ethanol was stirred at room temperature for 5 hr. The mixture was diluted with water, neutralized with 1 N hydrochloric acid, and extracted with methylene chloride. The methylene chloride solution was washed with water, dried over anhydrous sodium sulfate and concentrated at reduced pressure to give a yellow oil. Purification by column chromatography (silica gel, 35 g; ethyl acetate eluent) gave as the major component A as a foam. Crystallization from a mixture of ether and petroleum ether gave A as colorless crystals, mp 105°–107° C. assigned to be the 2-position isomer.

A later fraction gave a colorless oil which when treated with 2 mL of 1 M methanolic methanesulfonic acid gave B as fine yellow needles, mp 255°–257° C. assigned to the 3-position isomer.

EXAMPLE 27

5-Chloro-2'-fluoro-2-iodobenzhydrol

A mixture of 54 g (0.15 mole) of 5-chloro-2'-fluoro-2-iodobenzophenone and 28.4 g (0.75 mole) of sodium borohydride in 1000 ml of ethanol was stirred at 0° C. for 15 min. The solution was diluted with water and extracted with ether. The ether solution was washed with water, dried over anhydrous sodium sulfate, and concentrated at reduced pressure to give a deep yellow oil.

EXAMPLE 28

1-{4-Chloro-2-[(2-fluorophenyl)hydroxymethyl]phenyl}-3-phthalimidopropyne

The preparation of 1-{4-chloro-2-[(2-fluorophenyl)hydroxymethyl]phenyl}-3-phthalimidopropyne was conducted in the same manner as the preparation of 1-[4-chloro-2-benzoylphenyl]-3-phthalimidopropyne to give pale yellow prisms, mp 158°–160° C.

EXAMPLE 29

TABLET FORMULATION (Wet granulation)

| Item | Ingredients | mg/tablet | mg/tablet | mg/tablet | mg/tablet |
|---|---|---|---|---|---|
| 1. | 8-chloro-6-(2-chlorophenyl)-2H, 4H-[1,2,3]triazolo[4,5-d][2]benzazepine diluted with 8-chloro-6-phenyl-2H, 4H-[1,2,3]triazolo[4,5-d][2]benzazepine | 1 | 5 | 10 | 25 |
| 2. | Lactose | 202 | 232 | 261 | 280 |
| 3. | Modified Starch | 25 | 35 | 45 | 55 |
| 4. | Pregelatinized Starch | 20 | 25 | 30 | 35 |
| 5. | Distilled Water q.s. | — | — | — | — |
| 6. | Magnesium Stearate | 2 | 3 | 4 | 5 |
|  | Weight of tablet | 250 mg | 300 mg | 350 mg | 400 mg |

Procedure:
1. Mix Items 1–4 in a suitable mixer.
2. Granulate with sufficient distilled water to proper consistency. Mill.
3. Dry in a suitable oven.
4. Mill and mix with magnesium stearate for 3 minutes.
5. Compress on a suitable press equipped with appropriate punches.

EXAMPLE 30

TABLET FORMULATION (Direct compression)

| Item | Ingredients | mg/tablet | mg/tablet | mg/tablet | mg/tablet |
|---|---|---|---|---|---|
| 1. | 8-chloro-6-(2-chlorophenyl)-2H, 4H-[1,2,3]triazolo[4,5-d][2]benzazepine 8-chloro-6-phenyl-2H, 4H-[1,2,3]triazolo[4,5-d][2]benzazepine | 1 | 5 | 10 | 25 |
| 2. | Lactose | 221 | 217 | 212 | 181 |
| 3. | Avicel | 45 | 45 | 45 | 55 |
| 4. | Direct Compression Starch | 30 | 30 | 30 | 35 |
| 5. | Magnesium Stearate | 3 | 3 | 3 | 4 |
|  | Weight of tablet | 300 mg | 300 mg | 300 mg | 300 mg |

Procedure:
1. Mix Item 1 with an equal amount of lactose. Mix well.
2. Mix with Items 3, and 4, and the remaining amount of Item 2. Mix well.
3. Add magnesium stearate and mix for 3 minutes.
4. Compress on a suitable press equipped with appropriate punches.

EXAMPLE 31

CAPSULE FORMULATION

| Item | Ingredients | mg/tablet | mg/tablet | mg/tablet | mg/tablet |
|---|---|---|---|---|---|
| 1. | 8-chloro-6-(2-chlorophenyl)-2H, 4H-[1,2,3]triazolo[4,5-d][2]benzazepine 8-chloro-6-phenyl-2H, 4H-[1,2,3]triazolo[4,5-d][2]benzazepine | 1 | 5 | 10 | 25 |
| 2. | Lactose | 203 | 293.5 | 328 | 372.5 |
| 3. | Starch | 30 | 35 | 40 | 30 |
| 4. | Talc | 15 | 15 | 20 | 20 |
| 5. | Aerosol OT | 1 | 1.5 | 2 | 2.5 |
|  | Capsule fill weight | 250 mg | 350 mg | 400 mg | 450 mg |

Procedure:
1. Mill Items 1, 2, 3, and 5 in a suitable mixer. Mill.
2. Add talc and mix well.
3. Encapsulate on suitable equipment.

What is claimed:
1. A compound of the formula

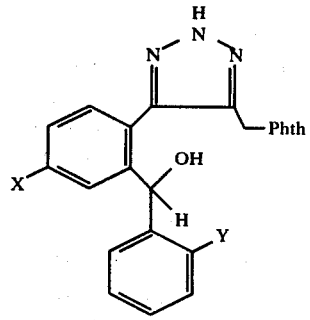

wherein X and Y are hydrogen or halogen.

* * * * *